United States Patent [19]

Seki et al.

[11] Patent Number: 5,534,502

[45] Date of Patent: Jul. 9, 1996

[54] PROCESS FOR PRODUCING FAT EMULSION

[75] Inventors: Junzo Seki, Hyogo; Hirofumi Yamamoto, Kyoto; Shuji Yamane, Kyoto; Yutaka Takahashi, Kyoto; Kouichi Ushimaru, Kyoto, all of Japan

[73] Assignee: Nippon Shinyaku Co. Ltd., Japan

[21] Appl. No.: 418,861

[22] Filed: Apr. 7, 1995

Related U.S. Application Data

[63] Continuation of Ser. No. 50,215, Jun. 21, 1993, abandoned.

[30] Foreign Application Priority Data

| Nov. 6, 1990 | [JP] | Japan | 2-301639 |
| Nov. 6, 1990 | [JP] | Japan | 2-301640 |

[51] Int. Cl.$^6$ ............ A61K 31/20; A61K 31/44; A61K 47/30; A61K 47/44
[52] U.S. Cl. ............ 514/31; 514/356; 514/359; 514/404; 514/538; 514/558; 514/762; 514/937; 514/943
[58] Field of Search ............ 514/356, 359, 514/404, 538, 558, 762, 937, 943, 31

[56] References Cited

U.S. PATENT DOCUMENTS

| 4,711,902 | 12/1987 | Serno | 514/356 |
| 4,784,845 | 11/1988 | Desai et al. | 424/80 |
| 5,229,422 | 7/1993 | Takahashi et al. | 514/558 |
| 5,236,955 | 8/1993 | Gordon | 514/557 |
| 5,244,925 | 9/1993 | Wretlind et al. | 514/777 |

FOREIGN PATENT DOCUMENTS

| 100459 | 2/1984 | European Pat. Off. . |
| 282405 | 9/1988 | European Pat. Off. . |
| 296845 | 12/1988 | European Pat. Off. . |
| 317120 | 5/1989 | European Pat. Off. . |
| 391369 | 10/1990 | European Pat. Off. . |
| 418153 | 3/1991 | European Pat. Off. . |
| 49-90705 | 8/1974 | Japan . |
| 53-56315 | 5/1978 | Japan . |
| 6416716 | 1/1989 | Japan . |
| 9102517 | 3/1991 | WIPO . |

*Primary Examiner*—Douglas W. Robinson
*Assistant Examiner*—Howard C. Lee
*Attorney, Agent, or Firm*—Graham & James

[57] ABSTRACT

Stable homogeneous fatty emulsions containing amphotericin B are prepared. According to one embodiment, amphotericin B is decrystallized using an acid and ethanol and then homogeneously dispersed in a lipid, following which it is emulsified.

According to a second embodiment, amphotericin B crystals are kneaded until their presence can no longer be confirmed and the decrystallized amphotericin B is thereafter uniformly dispersed in a lipid and, thereafter, emulsified.

8 Claims, No Drawings

PROCESS FOR PRODUCING FAT EMULSION

This application is a continuation of Ser. No. 08/050,215, filed Jun. 21, 1993, now abandoned.

TECHNICAL FIELD

The present invention relates to a technique for adding an effective amount of amphotericin B to a fatty emulsion during the process for the production of a fatty emulsion containing amphotericin B.

BACKGROUND ART

Even today, about 30 years after its development, amphotericin B is widely used as an important antifungal agent which may be administered to the entire body and which exhibits reliable effects. However, this substance causes serious side effects such as hemolytic toxicity and nephrotoxicity etc.

In recent years, the above-mentioned disadvantages of amphotericin B are being eliminated by its use as a liposomal preparation comprising a phospholipid, etc. or as a fatty emulsion prepared by emulsifying a simple lipid with a phospholipid.

It has been known that amphotericin B does not readily dissolve in such lipids. In the past, therefore, two methods have existed for the production of these preparations, which are (1) a method wherein amphotericin B and a lipid are added to a solvent such as chloroform, methanol, dimethylsulfoxide, etc., the solvent is removed after uniform solution, water is added thereto for emulsification, and (2) a method wherein amphotericin B is dissolved together with sodium deoxycholate in a solvent such as dimethylacetoamide, etc., and the solution is then added to a fatty emulsion. The disadvantages here are that in method (1), it is not possible to eradicate the possibility of the harmful solvent being left and in method (2), in addition to the same disadvantage of method (1), the irritative and hemolytic synthetic surfactant sodium deoxycholate, must necessarily be included in the preparation, and the amphotericin B is not completely encapsulated in the particles of the fatty emulsion.

In Japanese Patent Application Disclosure HEI 1-160915, a technique is disclosed for drying a liposomal preparation of amphotericin B after forming a composite of protonized distearoylphosphatidyl glycerol and amphotericin B beforehand in a mixture of chloroform and methanol, however, this requires the use of a harmful solvent during production, and residues thereof have caused major problems.

In light of these circumstances, the object of the present invention has been, from its inception, to obtain a stable, homogeneous fatty emulsion containing amphotericin B without the use of harmful substances during the production thereof.

DISCLOSURE OF THE INVENTION

As a result of avid research, we, the inventors of the present invention discovered that it is possible to achieve the above mentioned object using the production method described below.

The first gist of the present invention resides in a simple step during the production process of a fatty emulsion containing amphotericin B, wherein an acid and ethanol are used to decrystallize amphotericin B for its uniform dispersion in a lipid.

The second gist of the present invention resides in a simple step during the production process of a fatty emulsion containing amphotericin B, wherein amphotericin B is physically kneaded until the presence of amphotericin B crystals can no longer be confirmed, during the decrystallization of amphotericin B for its uniform dispersion in a lipid. Here, the term lipid is meant to include phospholipids and compound lipids.

The two inventions comprising the gists described above are separate and distinct, although their fields of industrial use and the problems they aim to overcome are the same.

An explanation will now be given regarding the first invention.

Based on the knowledge that amphotericin B does not readily dissolve in ethanol, we, the inventors of the present invention discovered that amphotericin B will dissolve very readily in ethanol if the ethanol is made acidic with an acid such as hydrochloric acid, etc., and thus the present invention was completed.

In order to fully disperse amphotericin B into the fatty emulsion component and stably encapsulate it in the fatty emulsion particles after its fine emulsification, it is necessary to disperse amphotericin B while in a amorphous state into the fatty emulsion component. In the amphotericin B fatty emulsion produced according to the present invention, the amorphous state of the amphotericin B was confirmed by X-ray analysis, etc.

According to the present invention, it is necessary to dissolve amphotericin B in ethanol.

The amount of ethanol used to dissolve the amphotericin B and that of the acid added thereto must be equal to or greater than the amounts required to fully dissolve the amphotericin B. However, excessive amounts thereof beyond what is necessary cannot be easily eliminated by the subsequent procedures, and therefore are not preferred. Generally, it is necessary to add 200 ml or more of ethanol to 1 g of amphotericin B. Preferably 300–800 ml, and more preferably 400–600 ml of ethanol is added.

When dissolving amphotericin B in ethanol according to the present invention, generally crystals of amphotericin B are first dispersed in the ethanol. For the dispersion, it is preferable to use a disperser such as an ultrasonic disperser or polytron homogenizer, etc. Thus, through the following procedure of addition of an acid for dissolution, it is possible to avoid decomposition of the amphotericin B even when it is in a large crystalline form which requires a long time for dissolution.

According to the present invention, after amphotericin B is dispersed in ethanol as described above, an acid is added thereto.

The acid used according to the present invention is not particularly limited, and examples thereof include inorganic acids such as sulfuric acid, nitric acid, phosphoric acid, etc., as well as organic acids such as citric acid, lactic acid, maleic acid, etc. Of these, hydrochloric acid is the most preferable.

Amphotericin B is relatively unstable in an acidic environment, and therefore it is not desirable to add the acid at a concentration above that which is necessary.

The amount of the acid to be added is 1–100 millimoles, preferably 2–20 millimoles, and more preferably 4–10 millimoles per 1 g of amphotericin B.

According to the present invention, acidic ethanol may be prepared in advance, and amphotericin B crystals may be added thereto for dissolution.

According to the present invention, a phospholipid or a mixture of a phospholipid and a simple lipid, etc. is added to the acidic ethanol solution of amphotericin B prepared as described above.

The amount of the phospholipid or the mixture of a phospholipid and a simple lipid to be added may be determined depending on the prescription for the desired fatty emulsion. In this case, the entire prescribed amount may be added, or a portion thereof may be added afterwards.

Generally, its proportion by weight is preferred to be 0.5 times that of amphotericin B or greater. More preferably, it may be used at between 0.5 times and 5 times, and even more preferably at 1–2 times the amount of amphotericin B.

If an overly excessive amount of a lipid is added, a long time will be required for the removal of the ethanol thereafter, and the subsequent drying process will produce a pasty form which is difficult to manage.

These lipids may be added in their original form to the acidic ethanol solution of amphotericin B, but they may also be added after being predissolved in an ethanol or acidic ethanol solution.

Amphotericin B is relatively unstable and readily decomposable under acidic conditions, and therefore it is preferable according to the present invention to neutralize the acid as soon as possible after mixing of the lipid with the acidic ethanol solution of amphotericin B.

The alkali used for neutralization is not particularly limited. For example, sodium hydroxide, potassium hydroxide, ammonia, triethylamine, etc. may be used. Sodium hydroxide is preferable to achieve the object of the present invention, as it forms sodium chloride upon neutralization of hydrochloric acid.

According to the present invention, the dissolution of amphotericin B may be effected at a low temperature. Amphotericin B is relatively unstable under acidic conditions, and therefore if the procedure is effected at a low temperature it is possible to prevent decomposition of the amphotericin B. In order to achieve this purpose, it is desirable to conduct the procedure at as low a temperature as possible, for example, at $-80°$ C.

According to the present invention, a drying procedure involving a conventional method such as lyophilization, spray drying, etc. may be used to remove the ethanol after neutralization.

In this manner, amphotericin B may be completely decrystallized to obtain a product which is substantially free of ethanol.

In addition, a precipitate formed after neutralization may be collected by filtration or centrifugation, and then dried. An excipient or filler may be pre-added thereto in cases where a paste results after drying which is difficult to manage.

Representative examples of such an excipient or filler include salts, sugars, proteins, polysaccharides and other macromolecules. Specific examples include sodium chloride, glucose, maltose, albumin, dextran, etc.

In addition to the drying procedure, a selectively permeable membrane (for example, a reverse osmosis membrane) may be used to remove the ethanol.

For the production of a fatty emulsion according to the present invention, water may be added after neutralization for coprecipitation of the amphotericin B and the added lipid.

Then, by washing with water, the sodium chloride produced during neutralization, as well as any residual acid or alkali, may be easily removed.

The product may also be dried, or used in its wet form and mixed with the other component lipids of the fatty emulsion. Further, if a selectively permeable porous membrane of an appropriate pore size is used, then desalting may be effected simultaneously with the removal of the ethanol.

The phospholipid or mixture of a phospholipid and a simple lipid containing amorphous amphotericin B, which is obtained in the above manner, may be emulsified according to a conventional known procedure for emulsification, with the addition of a desired additive and water.

The lipid containing amorphous amphotericin B obtained upon the removal of ethanol and drying according to the steps described above, or the coprecipitate obtained by the addition of water as described above, may be very easily mixed and homogenized with the phospholipid, simple lipid or a mixture thereof which are to be added thereafter as components of the fatty emulsion. This is one of the valuable effects of the present invention.

During the production of a fatty emulsion according to the present invention, the lipid, etc. may be easily mixed and homogenized during the emulsification process without heating which not only simplifies the procedure but also prevents decomposition of thermally unstable amphotericin B.

According to the present invention, the apparatus or equipment used for mixing or kneading is not particularly limited. A mortar or a polytron homogenizer, etc. may be used or even a common mixer/kneader often used for making ointments.

According to the present invention, a desired additive or water may be added for emulsification, without a procedure for removal of the ethanol. This is very useful in cases where ethanol is specified in the formula of the preparation.

A more detailed description of the second invention according to the present invention is given below.

According to the present invention, amphotericin B may be used in powder form.

According to the present invention, the above mentioned powdered amphotericin B may be kneaded together with the lipid by, for example, placing both into a vessel such as a mortar, etc. and physically kneading them with a pestle. The present invention may be effected by other methods, for example employing a kneader, etc. for normal industrial use. The apparatus or equipment used for kneading is not particularly limited. Devices commonly used for the production of ointments, etc. may be applied to carry out the present invention.

The conditions necessary and adequate to produce the effects of the present invention are understood to be complete mixing of the ingredients while applying a constant pressure, during the decrystallization of amphotericin B for its homogeneous dispersion in the lipid. The major gist of the present invention, as discovered by the inventors of the present invention, is the absence of any procedures other than those mentioned above for kneading.

An adequate amount of kneading according to the present invention will achieve the object in question, and therefore no other procedures are necessary. This type of physical kneading, if continuously employed, is known to gradually result in the decrystallization of amphotericin B, which may be confirmed by a conventional method of analysis. The kneading procedure according to the present invention is thus completed upon such confirmation.

The method of analysis may be, for example, X-ray analysis, observation by electron microscope or differential thermal analysis, etc.

Following the kneading procedure according to the present invention, it is possible to obtain a lipid containing amphotericin B, in liquid form or as a semi-solid paste substance. There is no need here for the addition of any solvent thereto.

For the production of a fatty emulsion according to the present invention, the above mentioned kneading procedure may be followed by a process which is normally used to produce fatty emulsions. For example, a phospholipid or a simple lipid may be added to and mixed with the above mentioned lipid containing amphotericin B, as an additional constituent of the fatty emulsion.

The amount of the phospholipid or the mixture of a phospholipid and a simple lipid to be added may be determined depending on the prescription for the desired fatty emulsion. In this case, the entire prescribed amount may be added, or a portion thereof may be added afterwards.

During the production of a fatty emulsion according to the present invention, a desired amount of water may be later added thereto and the mixture subjected to a usual coarse dispersion treatment followed by fine emulsification treatment. It is thus possible to obtain a homogeneous, stable fatty emulsion containing amphotericin B.

According to the present invention, the amount of the lipid added and the temperature thereof is understood to have an influence on the viscosity of the mixture. The simple lipid is preferably added at an amount of at least 2 times (proportion by weight) with respect to the amount of amphotericin B.

The amphotericin B crystals may thus be readily dispersed in the simple lipid to raise the efficiency of the mixing. The phospholipid is preferably added at an amount of at least 0.5 times or greater with respect to the amount of amphotericin B. If it is below this amount, it is difficult to achieve a uniform mixture. The amount of the phospholipid is even more preferably 1.0 times or greater.

According to the present invention, a mixture of simple lipid and phospholipid may be used. If the mixture consists of only phospholipid, then it is preferable to heat the mixture during the procedure.

The kneading of amphotericin B into the lipid according to the present invention is preferably effected at 70° C. or lower, as amphotericin B is unstable above this temperature. Also, at low temperatures of 10° C. or lower, the viscosity increases to become unsuitable for carrying out the present invention.

The thus prepared phospholipid or mixture of a phospholipid and a simple lipid containing decrystallized amphotericin B may be emulsified according to a conventional known procedure for emulsification, with the addition of a desired additive and water.

The object of the present invention may be achieved without the use of any organic solvent or synthetic surfactant, etc., thus eliminating all the disadvantages of their use as drugs due to residues thereof.

According to the present invention, amphotericin B may be homogeneously mixed beforehand with the constituents of the fatty emulsion, and therefore the amphotericin B can be stably encapsulated within the fatty emulsion particles even after fine emulsification.

According to the present invention, an appropriate amount of an acid may be added during the physical kneading. The addition of an acid is understood to significantly accelerate the homogeneity of the amphotericin B. If an acid is used, a necessary amount of an alkali (final pH preferably 4–8) to neutralize the acid is added after kneading.

The acid which may be appropriately used according to the present invention is not particularly limited. Examples thereof include inorganic acids such as hydrochloric acid, sulfuric acid, nitric acid and phosphoric acid, as well as organic acids such as citric acid, lactic acid, maleic acid, etc. Hydrochloric acid is particularly preferable. In addition, alkalis which may be used for neutralization afterwards include sodium hydroxide, potassium hydroxide, ammonia, triethylamine, etc. Sodium hydroxide is preferable, as it forms sodium chloride upon neutralization of hydrochloric acid.

If hydrochloric acid is used, a small amount thereof is acceptable, and addition of diluted hydrochloric acid at a concentration of 2–6 mole/l is preferable. Addition of large amounts of a highly diluted acid liberates water, which complicates kneading. Also, addition of a concentrated acid which raises the acidity to above that which is necessary is not preferred from the point of view of stability of amphotericin B. The total amount of the hydrochloric acid to be added differs greatly depending on the amounts of amphotericin B, soybean oil and phospholipids, but is generally preferred to be 10 millimoles or less per 1 gram of kneaded product.

The acid added in this manner has an accelerating effect on the homogeneity of the mixture, but it is not necessary for the main purpose of the present invention, which is to achieve homogeneity of amphotericin B in the lipid without the use of a solvent.

In both the first and second inventions according to the present invention, a fatty emulsion is produced using phospholipid and simple lipid.

The phospholipids available for use according to the present invention include phospholipids derived from, for example, egg yolk, soybean, cattle or pig, etc., or naturally occurring or semi-synthetic phospholipids, for example, phosphatidylcholine, phosphatidylethanolamine, phosphatidylserine, phosphatidylinositol, phosphatidylglycerol, etc. Specific examples include egg yolk phosphatidyl choline, soybean phosphatidyl choline, dipalmitoylphosphatidylcholine, dimyristoylphosphatidylcholine distearoylphosphatidylcholine, dioleoylphosphatidylcholine, dimyristoylphosphatidylglycerol, dipalmitoylph osphatidylglycerol, distearoylphosphatidylglycerol, etc., or their hydrogenated products. Of these, a preferred representative is refined egg yolk lecithin.

The simple lipids available for use according to the present invention include neutral lipids such as, for example, refined soybean oil, cottonseed oil, rapeseed oil, sesame oil, corn oil, peanut oil, safflower oil, triolein, trilinolein, tripalmitin, tristearin, trimyristin, triarachidonin, etc. Other examples include sterol derivatives such as cholestearyl oleate, cholesteryl linolate, cholesteryl myristate, cholesteryl palmitate, cholesteryl arachidate, etc. A representative example is refined soybean oil.

Also, in order to apply a surface charge to the fatty emulsion particles, a charged lipid, such as stearylamine, dicetyl phosphate, phosphatidic acid, phosphatidylglycerol, etc. may be used.

For the emulsification of the fatty emulsion containing amphotericin B according to the present invention, various conventional methods of producing fatty emulsions may be applied without modification. For example, it is common to employ a method wherein crude emulsification is effected with a homomixer, after which a pressurized spray type homogenizer such as a Manton-Gauline, a microfluidizer or ultrasonic homogenizer, etc. is used for adequate minuteness and formation. Here, a commonly known stearol, fatty acid, etc. or a derivative thereof may be added as a physiologically acceptable emulsifying adjuvant or stabilizer. Representative examples of these include fatty acids such as cholesterol or oleic acid, etc.

The shape and particle size of the fatty emulsion produced by the method according to the present invention may be easily confirmed using an electron microscope, a light scattering particle size analyzer or by filtration using a membrane filter.

The optional ingredients which may be used in the fatty emulsion preparation according to the present invention include additives, adjuvants, etc. which are conventionally used in injections. Examples thereof include antioxidants, antiseptics, stabilizers, isotonizing agents, buffers, etc. The necessary and optimum amounts of these additives, adjuvants, etc. may be varied as desired.

The fatty emulsion containing amphotericin B as obtained in the manner described above may be sterilized as necessary (for example, sterilization by filtration, high pressure steam sterilization, etc.) and encapsulated in an ampule with nitrogen gas. Or, it may be subjected to lyophilization as necessary. The lyophilized fatty emulsion containing amphotericin B may be renatured by the addition of an appropriate solution using a conventional method.

A preparation which comprises of a fatty emulsion containing amphotericin B as produced according to the present invention would commonly be administered intravenously to humans or various animals for the treatment or prevention of fungus or virus infection. In such a case, it is necessary to adequately control the size of the fatty emulsion particle etc. This is because, in general, if particles of 1 μm or greater are contained therein, various toxic results are known to occur, such as embolization of the capillaries, etc.

A fatty emulsion according to the present invention may be administered as necessary in the form of an intraarterial, intramuscular, intraspinal or subcutaneous injection, etc., in the same manner as for conventional drugs. Also it may be prepared and used as an eye drop, nose drop, oral medicine, inhalant, bladder infusion, external preparation or suppository, etc. In this case as well, a pharmaceutically acceptable additive such as a base, diluting agent, etc. may be used as an optional ingredient.

The dose of a preparation which comprises the fatty emulsion containing amphotericin B produced according to the present invention will differ depending on the route of administration, the form of the preparation, the symptoms of the patient and the desired purpose, but as a fatty emulsion is generally 1–1000 ml per administration. The dose of amphotericin B is generally 1–200 mg per administration for adults.

A fatty emulsion according to the present invention may, as necessary, be made into a lyophilized preparation suitable for storage. The method for the production of such a lyophilized preparation also falls within the technical scope of the present invention.

THE BEST MODE FOR CARRYING OUT THE INVENTION

Examples and tests relating to the method for the production of a fatty emulsion according to the present invention are provided below for a more detailed explanation of the present invention.

EXAMPLE 1

To 500 mg of raw amphotericin B crystals was added 250 ml of ethanol while cooling on ice, and an ultrasonic homogenizer was used for dispersion. To this dispersion was added 1.5 ml of 2N hydrochloric acid, and an ultrasonic homogenizer was used for dissolution. Separately, 50 ml of ethanol was added to 500 mg of refined egg yolk lecithin at room temperature, and an ultrasonic homogenizer was used for dispersion. To this solution was added 1.0 ml of 2N hydrochloric acid, and an ultrasonic homogenizer was used for dissolution. The solution was cooled on ice, and then adequately mixed with the above mentioned acidic ethanol solution of amphotericin B, and approximately 2.5 ml of 2N sodium hydroxide was added thereto to adjust the pH to 7.0.

The solution was then concentrated under reduced pressure after which 50 ml of water was added thereto, and the solution was further concentrated to dryness under reduced pressure. The coprecipitate was collected by centrifugation, repeatedly washed with water, and then lyophilized. Powder X-ray diffractometry confirmed the complete decrystallization of the amphotericin B in the obtained dried product.

To 6 mg of the lyophilized product containing amphotericin B were added 0.5 g of refined soybean oil and 0.497 g of refined egg yolk lecithin, and the mixture was kneaded to homogeneity. To the kneaded mixture was added 8 ml of an isotonic phosphate buffer solution, and stirring was effected with a homogenizer to produce a crude emulsified liquid. An additional amount of the isotonic phosphate buffer solution was then added to maintain a constant volume of 10 ml, after which the solution was emulsified for 60 minutes using an ultrasonic homogenizer (Branson Model 185) while cooling on ice, to obtain a super fine fatty emulsion containing amphotericin B. The emulsion was then subjected to a conventional method of lyophilization to obtain a lyophilized preparation.

EXAMPLE 2

To 100 mg of raw amphotericin B crystals was added 50 ml of ethanol while cooling on ice, and a polytron homogenizer was used for dispersion. To this dispersion was added 0.3 ml of 2N hydrochloric acid, and a polytron homogenizer was used for dissolution. Separately, 50 ml of ethanol was added to 500 mg of refined egg yolk lecithin at room temperature, and a polytron homogenizer was used for dispersion. To this solution was added 0.2 ml of 2N hydrochloric acid, and an ultrasonic homogenizer was used for dissolution. The solution was cooled on ice, and then adequately mixed with the above mentioned acidic ethanol solution of amphotericin B, and approximately 0.5 ml of 2N sodium hydroxide was added thereto to adjust the Ph to 7.0.

The solution was then concentrated under reduced pressure after which 50 ml of water was added thereto, and the solution was further concentrated under reduced pressure. The coprecipitate was collected by centrifugation, and repeatedly washed with water, after which 5 g of maltose was added thereto and the mixture was lyophilized. Powder X-ray diffractometry confirmed the complete decrystallization of the amphotericin B in the obtained dried product.

To an amount of the lyophilized product described above corresponding to 30 mg of amphotericin B were added 0.6 g of refined soybean oil and 0.47 g of refined egg yolk lecithin, and the mixture was kneaded, after which 8 ml of a 0.24M aqueous solution of glycerin was added thereto, and stirring was effected with a homogenizer to produce a crude emulsified liquid. An additional amount of the 0.24M aqueous solution of glycerin was then added to maintain a constant volume of 10 ml, after which the solution was emulsified for 60 minutes using an ultrasonic homogenizer (Branson Model 185) while cooling on ice, to obtain a super fine fatty emulsion containing amphotericin B. The emulsion was then subjected to a conventional method of lyophilization to obtain a lyophilized product.

EXAMPLE 3

To 10 g of raw amphotericin B crystals was added 20 l of ethanol while cooling on ice, and a polytron homogenizer was used for dispersion. To this dispersion was added 18.5 mg of citric acid, and a polytron homogenizer was used for dissolution. Separately, 30 g of refined egg yolk lecithin and 3 g of refined soybean oil were dissolved in 10 l of ethanol at room temperature using a polytron homogenizer. The solution was cooled on ice, and then adequately mixed with the above mentioned acidic ethanol solution of amphotericin B and 2N sodium hydroxide was added thereto to adjust the Ph to 7.0.

The solution was then concentrated under reduced pressure after which the coprecipitate was collected by filtration and repeatedly washed with water, and allowed to dry naturally. Powder X-ray diffractometry confirmed the complete decrystallization of the amphotericin B in the obtained dried product.

To an amount of the lyophilized product described above corresponding to 2 g of amphotericin B were added 20 g of refined soybean oil and 30 g of refined egg yolk lecithin, and the mixture was heated to approximately 60° C. while mixing, after which 100 ml of a 0.24M aqueous solution of glycerin was added thereto, and stirring was effected with a homomixer to produce a crude emulsified liquid.

The 0.24M aqueous solution of glycerin was then neutralized with sodium hydroxide, after which the solution was subjected to emulsification under high pressure using a microfluidizer, to obtain a super fine fatty emulsion containing amphotericin B. The emulsion was then subjected to a conventional method of lyophilization to obtain a lyophilized product.

EXAMPLE 4

To 10 mg of the wet coprecipitate obtained upon the filtration in Example 3 were added 0.5 g of cholestearyl oleate and 0.5 g of refined egg yolk lecithin, and mixing was effected. To this mixture was added 8 ml of a 0.24M aqueous solution of glycerin, and stirring was effected with a homogenizer to produce a crude emulsified liquid. After neutralizing the crude emulsified liquid using sodium hydroxide, the 0.24M aqueous solution of glycerin was added to maintain a constant volume of 10 ml, after which the solution was emulsified for 60 minutes using an ultrasonic homogenizer (Branson Model 185) to obtain a super fine fatty emulsion containing amphotericin B. The emulsion was then subjected to a conventional method of lyophilization to obtain a lyophilized product.

EXAMPLE 5

To 500 mg of raw amphotericin B crystals was added 250 ml of ethanol while cooling on ice, and an ultrasonic homogenizer was used for dispersion. To this dispersion was added 1.5 ml of 2N hydrochloric acid, and an ultrasonic homogenizer was used for dissolution. Separately, 50 ml of ethanol was added to 500 mg of dipalmitoylpho sphatidylglycerol at room temperature, and an ultrasonic homogenizer was used for dispersion. To this solution was added 1.0 ml of 2N hydrochloric acid, and an ultrasonic homogenizer was used for dissolution. The solution was cooled on ice, and then adequately mixed with the above mentioned acidic ethanol solution of amphotericin B, and approximately 2.5 ml of 2N sodium hydroxide was added thereto to adjust the Ph to 7.0.

The solution was concentrated using a reverse osmosis membrane, 5 g of refined soybean oil and 4 g of refined egg yolk lecithin were added thereto, and the mixture was mixed and kneaded. To the kneaded mixture was added 80 ml of a 10% aqueous solution of maltose, and stirring was effected with a homogenizer to produce a crude emulsified liquid. An additional amount of the 10% aqueous solution of maltose was then added to maintain a constant volume of 100 ml, after which the solution was emulsified for 60 minutes using an ultrasonic homogenizer (Branson Model 185) while cooling on ice, to obtain a super fine fatty emulsion containing amphotericin B. The emulsion was then subjected to a conventional method of lyophilization to obtain a lyophilized product.

EXAMPLE 6

To 500 mg of raw amphotericin B crystals was added 250 ml of ethanol while cooling on ice, and an ultrasonic homogenizer was used for dispersion. To this dispersion was added 2.5 ml of 2N hydrochloric acid, and an ultrasonic homogenizer was used for dissolution. To this solution was added 500 mg of refined egg yolk lecithin, and an ultrasonic homogenizer was used for adequate dissolution, after which approximately 2.5 ml of 2N sodium hydroxide was added thereto to adjust the pH to 7.0.

The solution was then concentrated under reduced pressure after which 50 ml of water was added thereto, and the solution was further concentrated under reduced pressure. The coprecipitate was collected by centrifugation, repeatedly washed with water, and then lyophilized. Powder X-ray diffractometry confirmed the complete decrystallization of the amphotericin B in the obtained dried product.

The obtained dried product (an amount corresponding to 3 mg of amphotericin B) and 0.4 g of refined egg yolk lecithin were placed in a mortar, mixed and kneaded. To the kneaded mixture were added 0.5 g of refined soybean oil and 8 ml of a 9% aqueous solution of lactose, and stirring was effected with a homogenizer to produce a crude emulsified liquid. An additional amount of the 9% aqueous solution of lactose was then added to maintain a constant volume of 10 ml, after which the solution was emulsified for 60 minutes using an ultrasonic homogenizer (Branson Model 185), to obtain a super fine fatty emulsion containing amphotericin B. The emulsion was then subjected to a conventional method of lyophilization to obtain a lyophilized product.

EXAMPLE 7

A portion of 170 mg of the dried product obtained in Example 2, 0.5 g of refined soybean oil, 0.4 g of hydrogenated egg yolk lecithin and 0.1 g of cholesterol were placed in a mortar, mixed and kneaded. To this kneaded mixture was added 8 ml of a 9% aqueous solution of lactose, and stirring was effected with a homogenizer to produce a crude emulsified liquid. An additional amount of the 9% aqueous solution of lactose was then added to maintain a constant volume of 10 ml, after which the solution was emulsified for 60 minutes using an ultrasonic homogenizer (Branson Model 185) to obtain a super fine fatty emulsion containing amphotericin B. The emulsion was then subjected to a conventional method of lyophilization to obtain a lyophilized product.

Test Example 1: Measurement of particle size

The sizes of the particles of the fatty emulsions containing amphotericin B which were obtained in Examples 1–7 were evaluated by laser using a dynamic light scattering particle size analyzer, and the following results were obtained. No particles with a size of 1 μm or greater were found.

| Example No. | Mean particle size | Example No. | Mean particle size |
| --- | --- | --- | --- |
| 1 | 47 nm | 5 | 47 nm |
| 2 | 70 nm | 6 | 45 nm |
| 3 | 23 nm | 7 | 61 nm |
| 4 | 52 nm | | |

EXAMPLE 8

Three grams of refined egg yolk lecithin was added to 3 g of amphotericin B crystals, and the mixture was adequately mixed and kneaded for 10 minutes using an agate mortar. Powder X-ray diffractometry confirmed the complete decrytstallization of the amphotericin B in the obtained kneaded product. To 6 mg of the kneaded product containing amphotericin B were added 0.5 g of refined soybean oil and 0.497 g of refined egg yolk lecithin, and kneading was further effected for homogeneity. To the kneaded product was added 8 ml of an isotonic phosphate buffer solution, and stirring was effected with a homogenizer to produce a crude emulsified liquid. An additional amount of the isotonic phosphate buffer solution was then added to maintain a constant volume of 10 ml, after which the solution was emulsified for 60 minutes using an ultrasonic homogenizer (Branson Model 185) while cooling on ice, to obtain a super fine fatty emulsion containing amphotericin B.

The emulsion was then subjected to a conventional method of lyophilization to obtain a lyophilized product.

EXAMPLE 9

To 0.1 g of amphotericin B crystals was added 0.1 g of refined egg yolk lecithin, and the mixture was adequately premixed and kneaded for 10 minutes using an agate mortar. To the kneaded product was added 0.5 ml of 2N hydrochloric acid, and the mixture was immediately mixed and kneaded. Power X-ray diffractometry confirmed the complete decrystallization of the amphotericin B in the obtained kneaded product. To an amount of the kneaded product obtained above corresponding to 30 mg of amphotericin B were added 0.6 g of refined soybean oil and 0.47 g of refined egg yolk lecithin, and kneading was further effected, after which 8 ml of a 0.24M aqueous solution of glycerin was added thereto, and stirring was effected with a homogenizer to produce a crude emulsified liquid. The solution was neutralized with 0.5 ml of 2N sodium hydroxide, after which an additional amount of the 0.24M aqueous solution of glycerin was added to maintain a constant volume of 10 ml, and the solution was emulsified for 60 minutes using an ultrasonic homogenizer (Branson Model 185) while cooling on ice, to obtain a super fine fatty emulsion containing amphotericin B. The emulsion was then subjected to a conventional method of lyophilization to obtain a lyophilized product.

EXAMPLE 10

15 g of refined egg yolk lecithin was added to 10 g of amphotericin B crystals, and the mixture was pre-mixed and kneaded using a mortar. To the kneaded product was added 20 ml of 6N hydrochloric acid, and the mixture was immediately mixed and kneaded using a polytron homogenizer Power X-ray diffractometry confirmed the complete decrystallization of the amphotericin B in the obtained kneaded product. To an amount of the kneaded product obtained above corresponding to 2 g of amphotericin B were added 20 g of refined soybean oil and 30 g of refined egg yolk lecithin, and the mixture was heated to approximately 60 for mixing, after which 100 ml of a 0.24M aqueous solution of glycerin was added thereto, and stirring was effected with a homomixer to produce a crude emulsified liquid. The crude emulsified solution was neutralized with sodium hydroxide, after which it was subjected to emulsification under high pressure using a microfluidizer to obtain a super fine fatty emulsion containing amphotericin B. The emulsion was then subjected to a conventional method of lyophilization to obtain a lyophilized product.

EXAMPLE 11

To 4 mg of the kneaded product obtained in Example 10 were added 0.5 g of cholestearyl oleate and 0.5 g of refined egg yolk lecithin, and mixing was effected. To this was added 8 ml of a 0.24M aqueous solution of glycerin, and stirring was effected with a homogenizer to produce a crude emulsified liquid. This was neutralized with sodium hydroxide, after which an additional amount of the 0.24M aqueous solution of glycerin was added to maintain a constant volume of 10 ml, and the solution was emulsified for 60 minutes using an ultrasonic homogenizer (Branson Model 185) to obtain a super fine fatty emulsion containing amphotericin B. The emulsion was then subjected to a conventional method of lyophilization to obtain lyophilized product.

EXAMPLE 12

20 mg of refined soybean oil was added to 3 mg of amphotericin B crystals, and the mixture was adequately mixed and kneaded to homogeneity for about 10 minutes using an agate mortar. To the kneaded mixture were added 0.5 g of refined soybean oil, 0.4 g of refined egg yolk lecithin and 0.1 g of dimyristoylphosphatidylglycerol, and mixing and kneading was further effected. To this was added 8 ml of a 10% aqueous solution of maltose, and stirring was effected with a homogenizer to produce a crude emulsified liquid. An additional amount of the 10% aqueous solution of maltose was then added to maintain a constant volume of 10 ml, after which the solution was emulsified for 60 minutes using an ultrasonic homogenizer (Branson Model 185) to obtain a super find fatty emulsion containing amphotericin B. The emulsion was then subjected to a conventional method of lyophilization to obtain a lyophilized product.

EXAMPLE 13

3 mg of amphotericin B, 0.5 g of refined soybean oil, 0.4 g of hydrogenated egg yolk lecithin and 0.1 g of cholesterol were placed in a mortar, and adequately mixed and kneaded for about 20 minutes. Powder X-ray diffractometry confirmed the complete decrystallization of the amphotericin B in the obtained kneaded product. 8 ml of a 9% aqueous solution of lactose was added thereto, and stirring was effected with a homogenizer to produce a crude emulsified liquid. An additional amount of the 9% aqueous solution of lactose was then added to maintain a constant volume of 100 ml, after which the solution was emulsified for 60 minutes using an ultrasonic homogenizer (Branson Model 185) to obtain a super fine fatty emulsion containing amphotericin B. The emulsion was then subjected to a conventional method of lyophilization to obtain a lyophilized product.

EXAMPLE 14

20 mg of refined soybean oil was added to 300 mg of amphotericin B crystals, and this was adequately mixed and kneaded to homogeneity for about 10 minutes using a vacuum grinder. To the kneaded mixture were added 50 g of refined soybean oil, 40 g of refined egg yolk lecithin and 1 g of dimyristoylphosphatidylglycerol, and mixing and kneading was further effected. To the mixture was added 800 ml of a 10% aqueous solution of maltose, and stirring was effected with a homogenizer to produce a crude emulsified liquid. The 10% aqueous solution of maltose was then added to maintain a constant volume of 1000 ml, after which the solution was emulsified for 60 minutes using a pressure homogenizer (product of Nippon Seiki Co.) to obtain a super fine fatty emulsion containing amphotericin B. The emulsion was then subjected to a conventional method of lyophilization to obtain a lyophilized product.

EXAMPLE 15

To 3 mg of amphotericin B crystals was added 0.1 g of dimyristoylphosphatidylglycerol, and then 0.1 ml of 2N hydrochloric acid was added thereto and an agate mortar was used for mixing and kneading to homogeneity. To this kneaded mixture were added 0.5 g of refined soybean oil and 0.4 g of refined egg yolk lecithin, and mixing and kneading were further effected. To the resulting mixture was added 8 ml of a 10's aqueous solution of maltose, and stirring was effected with a homogenizer to produce a crude emulsified liquid. The solution was neutralized with 2N sodium hydroxide, after which a 10% aqueous solution of maltose was then added to maintain a constant volume of 10 ml, and the solution was emulsified for 60 minutes using an ultrasonic homogenizer (Branson Model 185) to obtain a super fine fatty emulsion containing amphotericin. The emulsion was then subjected to a conventional method of lyophilization to obtain a lyophilized product.

Test Example 2: Measurement of particle size

The sizes of the particles of the fatty emulsions containing amphotericin a which were obtained in Examples 8–15 were evaluated by laser using a dynamic light scattering particle size analyzer, and the following results were obtained. No particles with a size of 1 μm or greater were found.

| Example No. | Mean particle size | Example No. | Mean particle size |
|---|---|---|---|
| 8 | 45 nm | 12 | 48 nm |
| 9 | 93 nm | 13 | 31 nm |
| 10 | 20 nm | 14 | 52 nm |
| 11 | 55 nm | 15 | 48 nm |

We claim:

1. A process for preparing a fatty emulsion containing Amphotericin B in a fatty emulsion particle that is comprised of a phospholipid and a simple lipid, which process comprises the steps of:

a. dissolving Amphotericin B and a member of the group consisting of the phospholipid and the mixture of the phospholipid and the simple lipid, wherein the amount of said member of the group being dissolved is part of or entirely a predetermined amount; in ethanol, acidified with an acid compatible with the ethanol and Amphotericin B;

b. neutralizing the acid with an alkali, compatible with the ethanol and Amphotericin B;

c. removing the ethanol, to leave a product containing Amphotericin B and phospholipid or the mixture of phospholipid and simple lipid; and d. adding sufficient additional phospholipid or simple lipid or both phospholipid and simple lipid, if needed, to reach said predetermined amount; and water thereto; and e. emulsifying the combination.

2. A process according to claim 1, wherein the ethanol is acidified prior to the addition of the Amphotericin B thereto.

3. A process according to claim 1 wherein the acid is selected from the group consisting of sulfuric acid, phosphoric acid, citric acid, lactic acid, maleic acid and hydrochloric acid.

4. A process according to claim 1, wherein the amount of ethanol is 300 to 800 ml per gram of Amphotericin B and the amount of acid is 1 to 100 millimoles per gram of Amphotericin B.

5. A process according to claim 1, wherein the alkali is selected from the group consisting of sodium hydroxide, potassium hydroxide, ammonia and trimethylamine.

6. A process for preparing a fatty emulsion containing Amphotericin B in a fatty emulsion particle that is comprised of a phospholipid and a simple lipid, which process comprises the steps of:

a. kneading powdered Amphotericin B with the phospholipid or a mixture of the phospholipid and the simple lipid until the Amphotericin B crystals can no longer be confirmed, wherein the amount of said phospholipid or phospholipid and simple lipid is part of or entirely a predetermined amount;

b. adding sufficient additional phospholipid or simple lipid or both phospholipid and simple lipid, if needed, to reach said predetermined amount; and water thereto, and emulsifying the combination.

7. A process according to claim 1, wherein the phospholipid is egg yolk lecithin and the simple lipid is soybean oil.

8. A process according to claim 6, wherein the phospholipid is egg yolk lecithin and the simple lipid is soybean oil.

* * * * *